(12) United States Patent
Stusak

(10) Patent No.: US 7,057,197 B2
(45) Date of Patent: Jun. 6, 2006

(54) METHOD AND DEVICE FOR CONTACTLESS MEASUREMENT OF A LINEAR TEXTILE FORMATION SUCH AS YARN ETC

(75) Inventor: Miroslav Stusak, Brandys nad Orlici (CZ)

(73) Assignee: Rieter CZ a.s. (CZ)

( * ) Notice: Subject to any disclaimer, the term of this patent is extended or adjusted under 35 U.S.C. 154(b) by 61 days.

(21) Appl. No.: 10/415,581

(22) PCT Filed: Oct. 31, 2001

(86) PCT No.: PCT/CZ01/00059

§ 371 (c)(1),
(2), (4) Date: Oct. 22, 2003

(87) PCT Pub. No.: WO02/37054

PCT Pub. Date: May 10, 2002

(65) Prior Publication Data

US 2004/0051058 A1 Mar. 18, 2004

(30) Foreign Application Priority Data

Nov. 2, 2000 (CZ) .............................. PV 4070-00

(51) Int. Cl.
*G01B 11/10* (2006.01)
(52) U.S. Cl. .................................................. 250/559.4
(58) Field of Classification Search .. 356/238.1–238.2, 356/239.1; 250/559.27, 559.45, 559.01
See application file for complete search history.

(56) References Cited

FOREIGN PATENT DOCUMENTS

| DE | 19532767 A1 | 3/1997 |
| EP | 0112475 A1 | 7/1984 |
| GB | 2064106 A | 6/1981 |
| GB | 2064106 A * | 6/1981 |
| WO | WO 9936746 A1 | 7/1999 |

OTHER PUBLICATIONS

PCT International Preliminary Examination Report, Mar. 22, 2002.

* cited by examiner

*Primary Examiner*—David Porta
*Assistant Examiner*—Tony Ko
(74) *Attorney, Agent, or Firm*—Dority & Manning, P.A.

(57) ABSTRACT

The invention relates to the contactless measurement of a linear textile formation such as yarn, thread, textile fiber, sliver, etc. in which a linear textile formation moves in a radiation flux between a radiation source and a radiation sensor consisting of a plurality of radiation-sensitive elements arranged next to each other in at least one row and in which the diameter and/or the hairiness and/or the density of the linear textile formation is determined on the basis of the number of overshadowed radiation-sensitive elements of the radiation sensor and/or on the basis of the irradiation degree of the radiation-sensitive elements. In order to measure a high degree of the total length of the moving textile formation it is proposed to match the dimensions of the radiation-sensitive elements such that the dimension of the radiation-sensitive elements of the radiation sensor in the direction of the motion of the measured linear textile formation is superior to their dimension in the direction normal to the direction of the motion of the measured linear textile formation.

4 Claims, 2 Drawing Sheets

METHOD AND DEVICE FOR CONTACTLESS MEASUREMENT OF A LINEAR TEXTILE FORMATION SUCH AS YARN ETC

FIELD OF THE INVENTION

The invention relates to a device for contactless measurement of parameters of a linear textile formation (1) such as yarn, thread, textile, fiber, silver, etc. The device includes a radiation source, a radiation sensor which has a plurality of radiation-sensitive elements arranged in at least one row, and an evaluation device connected with the radiation sensor. The device also has an output of information on the monitored parameters of the linear textile formation. The device is arranged in such a manner that the linear textile formation is movable along its longitudinal axis in the direction of its motion and is movable in the radiation flux between the radiation source and the radiation sensor with the row of radiation-sensitive elements being arranged perpendicular to the direction of motion.

BACKGROUND OF THE INVENTION

WO 99/36746 discloses a device for contactless measurement of parameters of a linear textile formation such as yarn, thread, textile fiber, silver, etc. in which a linear textile formation moves in a radiation flux between a radiation source and a radiation sensor consisting of a plurality of radiation-sensitive elements arranged next to each other in a row. The device determines the diameter and/or the hairiness and/or the density etc. of the linear textile formation on the basis of the number of overshadowed radiation-sensitive elements. The radiation sensors used are CCD sensors sensing the linear textile formation discontinuously in very short sections, each of about 10 µm of its length.

The drawback consists in that as a matter of fact only a minimum of the total length of the linear textile formation is really measured. The values determined on the very short sections of the measured linear textile formation, for instance, when measuring yarn thickness have to be integrated in a complicated way prior to the processing proper in order to eliminate or at least to minimize the influence of coincidental events arising during the measurement of the very short sections of the linear textile formation and so to achieve the required measurement precision of the parameters of the linear textile formation. This is due to the fact that the yarn moves at a given velocity such as 1 m.s$^{-1}$ whereas the current sensing velocity of the linear textile formation by means of CCD sensors is about 1× in 1 ms. Since the radiation-sensitive elements of CCD sensors used for contactless measurement of a linear textile formation are about 10 µm×10 µm in size, this measurement device, when applied to a linear textile formation moving, for instance, at 1 m.s-1 effectively manage to measure as little as 1% of the total length of the linear textile formation which especially nowadays has proved to be insufficient.

DE 195 32 767 A1 and EP 0 112 475 A1 disclose radiation sensors whose radiation-sensitive elements are shaped rectangularly and whose length is superior to their width. However, in view of both the dimensions of the radiation-sensitive elements which are in EP 0 122 475 A1 in the order of millimeters and of the design of the sensors, these sensors are unfit for use in the measurement of the parameters of a linear textile formation such as yarn, thread, textile fiber, silver, etc.

OBJECTS AND SUMMARY OF THE INVENTION

For the reasons above a principal object of the invention is to develop a device for contactless measurements of a linear textile formation permitting virtually to measure a larger part of the length of the linear textile formation in relation to the total length of the linear textile formation and at the same time permitting a simple processing of the measurement results. Additional objects and advantages of the invention will be set forth in part in the following description, or may be obvious from the description, or may be learned through practice of the invention.

The aim of the invention has been reached by a device for contactless measurement of parameters of a linear textile formation such as yarn, thread, textile fiber, silver, etc., having rectangular-shaped radiation-sensitive elements with dimensions in the direction of motion of the linear textile formation superior to their dimensions perpendicular to the direction of motion.

Due to this, in each row of radiation-sensitive elements, the information on the properties of the measured linear textile formation is at a given measurement instant determined on a length section of the linear textile formation whose length is superior to the dimension of radiation-sensitive elements of this row of radiation sensitive elements in the direction normal to the direction of the motion of the linear textile formation. Thus, on the one hand, the virtual measurement of a greater portion of the measurement linear textile formation is obtained while maintaining the measurement velocity and, on the other hand, the necessity of integrating individual values determined by the radiation sensor during the measurement of the thickness of the linear textile formation is dispensed with, thereby simplifying the processing of the measurement results.

An advantage of the invention exists in the fact that the measurement proper of the linear textile formation, i.e., without the subsequent integration of the individual values found by measurement, furnishes a value which by its character better reflects the actual parameters of the measured linear textile formation. This advantage permits an increase in the processing speed of individual measurements and simplifies the calculation algorithms for evaluating the measurement and interpreting the measurement results, thus reducing the requirements put on the device for measurement evaluation.

The device arranged in this way is easy to produce and to control, reliable in operation, and sufficient in precision. Another advantage of this device is in the increased surface of the radiation-sensitive elements of the radiation sensor as compared with the radiation-sensitive elements used in other radiation sensors. This advantage reduces the sensitivity of the radiation sensors to negative influences due to dust and permits a better-defined base point of the radiation-sensitive elements if such a base point exists and is required. Another advantage is the increased light sensitivity advantageously permitting, while maintaining the irradiation intensity of the sensor used in known sensors, the carrying out of measurements at speeds superior to those obtainable in measurements using square-shaped radiation-sensitive elements.

In one preferred embodiment, the radiation sensor is made as a CMOS optical sensor.

In another preferred embodiment, the radiation sensor consists of a CCD sensor.

Each of the two types of the radiation sensor is sufficiently precise and reliable for the device according to the invention. The advantage of the CMOS optical sensors over the CCD sensors consists in a more favorable measurement speed, in a more suitable and therefore more easily processable output signal, easier manufacture, and lower purchase cost. However, in spite of some drawbacks of the CCD sensors as compared with the CMOS optical sensors, the device equipped with the CCD sensor is sufficiently reliable and fully operative.

For obtaining the required measurement precision with sufficiently small size of the radiation-sensitive elements, it is advantageous if the radiation-sensitive elements are shaped as rectangular with dimensions in the direction of the motion of the measured linear textile formation between 15 µm and 200 µm.

From the point of view of simplicity of the arrangement of the device for the contactless measurement of the linear textile formation with sufficient measurement precision and simplicity of processing of the signals of the radiation sensor, it is advantageous if the radiation sensor contains one row of radiation-sensitive elements.

For obtaining high measurement precision involving, however, higher time consumption and higher requirements put on the device for the processing of the measured data, it is advantageous if the radiation sensor comprises at least two rows of radiation-sensitive elements with the neighboring rows of radiation-sensitive elements mutually reset in the direction normal (perpendicular) to the direction of motion of the measured linear textile formation.

From the point of view of optimizing the relation between the high precision of the measuring of the linear textile formation on the one side and the required amount of time consumption and requirements put on the device for processing the measured data on the other side, it is advantageous if the radiation sensor comprises exactly two rows of radiation-sensitive elements mutually reset in the direction normal (perpendicular) to the direction of motion of the measured linear textile formation by one half of their dimension in this direction.

DETAILED DESCRIPTION

Reference will now be made in detail to the presently presented embodiments of the invention, one or more examples of which are shown in the figures. Each example is provided to explain the invention, and not as a limitation of the invention. In fact, features illustrated or described as part of one embodiment can be used with another embodiment to yield still a further embodiment. It is intended that the present invention cover such modifications and variations.

The contactless measurement of a linear textile formation such as yarn, thread, textile fiber, sliver, etc., is carried out on various textile machine types such as open-end spinning machines, winding machines, etc.

Figure 1:
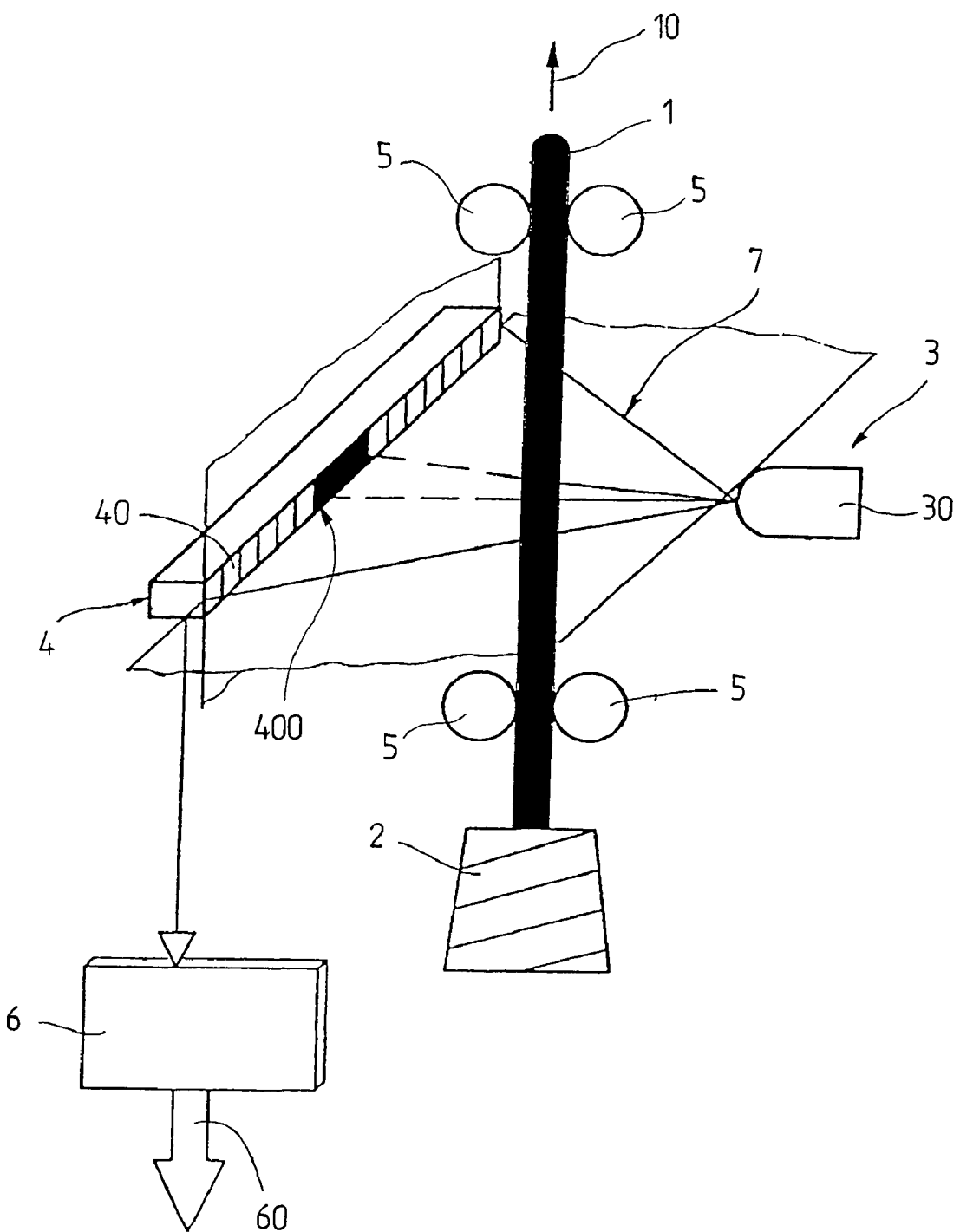
FIG. 1 shows a schematic of the arrangement for contactless measurement of a linear textile formation.
Figure 2:
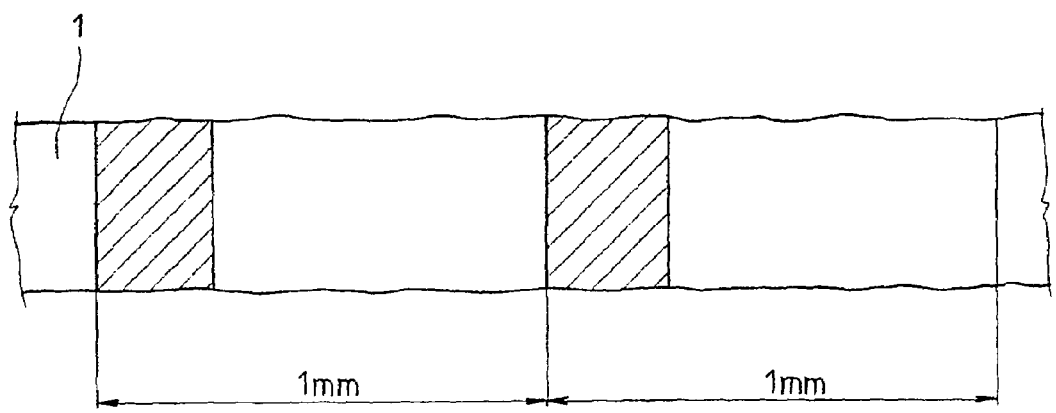
FIG. 2 shows a lateral view of the measured linear textile formation with marked sections of the measured linear textile formation which are at each measurement sensed by the radiation sensor.

In the shown example of FIG. 1, the device for contactless measurement of a linear textile formation is used on an open-end spinning machine for measuring a yarn 1. However, the device can be suitably modified for use on other textile machines and for the measurement also of linear textile formations other than the yarn 1, such possible modification having no influence on the principle of the invention.

In the shown example of embodiment, the yarn 1 is drawn off from a spinning device 2 in the direction of the arrow 10 and is wound by a not illustrated winding device on a not illustrated bobbin. On its path between the spinning device 2 and the winding device, the yarn 1 passes through the space between a radiation source 3 and a radiation sensor 4. In the shown example of embodiment, the travel path of the yarn 1 is stabilized by a pair of guiding rollers 5. In other embodiments, the guiding of the yarn 1 in the space between the radiation source 3 and the radiation sensor 4 is ensured by other suitable means such as fix guides. In still another example of embodiment, no guiding elements are provided for guiding the yarn 1 in the space between the radiation source 3 and the radiation sensor 4.

In the shown example of embodiment, the radiation source 3 is made as a point source 30 of radiation of a suitable type such as LED, LASER, a bulb, etc. In a not shown example of another embodiment, the radiation source 3 can be of another suitable type such as a straight-line radiation source or even a flat radiation source.

In the shown embodiment, the radiation sensor 4, situated opposite the radiation source 3, contains one row of radiation-sensitive elements 40 situated next to each other. In another embodiment, the radiation sensor 4 contains at least two rows of radiation-sensitive elements 40 situated next to each other, and the total number of rows of the radiation-sensitive elements 40 situated next to each other can be even greater. However, between each two neighboring radiation-sensitive elements 40, there are sections (intervals) in which the measured linear textile formation cannot be followed, because the neighboring radiation-sensitive elements 40 are physically (materially) separated there. In standard measurements, the existence of these intervals is from the point of view of the measurement precision immaterial but, for extremely high precision requirements this drawback should be eliminated, for instance, by arranging the rows of the radiation sensor 4 with more than one row of radiation-sensitive elements 40 in the direction normal (perpendicular) to the direction of motion of the measured linear textile formation. Thus, for instance, in a radiation sensor 4 with two rows of radiation-sensitive elements 40 reset to each other and normal to the direction of motion of the measured linear textile formation, each row of the radiation-sensitive elements 40 senses the measured linear textile formation also in the above mentioned sections (intervals) between the radiation-sensitive elements 40 of the other row of the radiation-sensitive elements 40. This mutual reset preferably equals in size one half of the dimension of one of the radiation-sensitive elements 40 in the direction normal to the direction of motion of the measured linear textile formation. In the direction of the length of the row of the radiation-sensitive elements 40, the radiation sensor 4 is situated across the direction of motion of the measured linear textile formation such as the yarn 1, and the dimension of the individual radiation-sensitive elements 40 in the direction of motion of the measured linear textile formation, i.e., in the longitudinal direction of the linear textile formation, is superior to their dimension in the direction transverse to the direction of motion of the yarn 1, i.e., in the direction of the length of the row of the radiation-sensitive elements 40. However, the dimension of the radiation-sensitive elements 40 in the direction of motion of the measured linear textile formation is inferior to the length of the smallest defect of the measured linear textile formation required to be detected.

From the point of view of the optimizing of the relation between the required measurement precision and the cost of the constituting elements of the measurement device, in particular of the radiation sensors 4, it is as a rule sufficient for the individual radiation-sensitive elements 40 to be sized between 15 μm and 200 μm in the direction of motion of the measured linear textile formation. The radiation sensor 4 can consist of a CMOS optical sensor or of a CCD sensor. Each of the rows of the radiation-sensitive elements 40 of the radiation sensor 4 is coupled with an evaluation device 6 of the state and/or degree of its irradiation. In a further embodiment, the evaluation device 6 can be made as an integral part of the radiation sensor 4. The measured linear textile formation, in the shown embodiment, the yarn 1, passes during the measurement through a radiation flux 7 emitted by the radiation source 3 and casts shadow on some of the radiation-sensitive elements 40 of the radiation sensor 4 as is in the shown example of embodiment marked by the dark surface 400 on the front side of the radiation sensor 4. The number of irradiated radiation-sensitive elements 40 and/or the degree of their irradiation serves as basis for determining in a suitable way the required parameters of the measured linear textile formation such as the yarn 1. In other words, the evaluation device 6 is able to evaluate the function of the radiation sensor 4 and is fitted with an output 60 of information on the monitored parameters of the measured linear textile formation such as the yarn 1, for instance, on the thickness of the yarn 1, or the hairiness of the yarn 1, etc. As required by specific needs of a given case, the output 60 can be connected with further information-processing devices including, for instance, a control system of the machine or the operating unit and/or a displaying device and/or a recording device and/or regulation means of the operating unit of the machine and/or control means of the operating unit, used to interrupt the moving yarn and/or to stop at least one of the functional elements of the operating unit of the machine, etc.

In another embodiment, the contactless measurement device for the linear textile formation can be fitted or coupled with a suitable device for controlling the radiation emitted by the radiation source 3 to more exactly control both the intensity of the radiation and, in discontinuous radiation source, the time course of the radiation.

The contactless measurement of the linear textile formation such as the yarn 1, thread, textile fiber, sliver, etc., takes place with the linear textile formation moving in the radiation flux 7 in the space between the radiation source 3 and the radiation sensor 4. The linear textile formation takes a part of the radiation flux 7 and thus casts shadow on some of the radiation-sensitive elements 40 of the radiation sensor 4. At predetermined time intervals, the radiation source 4 carries out individual measurements of the linear textile formation, each time on a portion of the length of the linear textile formation as a rule superior to 15 μm. Consequently, if the measured linear textile formation moves at 1 m.s$^{-1}$ and the parameters of the linear textile formation are measured at a speed of 1× in 1 ms, each time on a length of the linear textile formation as a rule superior to 15 μm. This measurement method virtually covers at least 1.5% of the total length of the measured linear textile formation as compared with 1% obtained by the methods of the state of the art at the same speed of measurement and of motion of the linear textile formation which represents an increase in the virtually measured length of the linear textile formation by at least 50% as compared with the same measurement carried out by existing methods and means. With larger dimensions of the radiation-sensitive elements 40 in the direction of motion of the measured linear textile formation, the above improvement on the virtual measurement of the length portion of the measured linear textile formation is still greater with all accompanying positive consequences. Thus, for instance, if the radiation sensor 4 used for the measurement of a linear textile formation is fitted with radiation-sensitive elements 40 200 μm long in the direction of motion of the measured linear textile formation and if the measured linear textile formation moves at a speed of 1 m.s$^{-1}$ and the measurement speed is 1× in 1 ms, then a section of 200 μm is measured each time so that the virtual measurement of the parameters of the linear textile formation comprises 20% of its total length as compared with 1% currently reached at present at the same speed of both the measurement and of the motion speed of the measured linear textile formation. This is an increase by 2000% in the virtually measured length of the linear textile formation as compared with the same measurement carried out by existing methods and means. In addition to this, each measurement of the linear textile formation on the greater length furnishes sufficiently integrated values of the sensed parameters of the linear textile formation, for instance, the values of thickness of the yarn 1 because each such sensing of the parameters of the linear textile formation has by itself the character of the formerly required additional machine integration of a number of separately measured values on not more than 10 μm long sections of the linear textile formation. After the carried out measurement of the linear textile formation, the obtained values are further used in a suitable way for processing and/or displaying and/or evaluating the measurement and/or for interpreting the measurement results.

The device for contactless measurement of the linear textile formation such as the yarn 1, thread, textile fiber, sliver, etc., can be on each operating unit of the textile machine in question controlled by a control unit of the operating unit which can also evaluate and process the measured values of the parameters of the measured linear textile formation.

In case of a radiation sensor 4 fitted with matrix configuration of radiation-sensitive elements 40, the required surface of the radiation sensor 4 contains a smaller number of radiation-sensitive elements as compared with the presently used radiation sensors with square plain view profile of the radiation-sensitive elements which results in lower costs of the radiation sensor according to the invention as compared with the existing radiation sensors fitted with matrix configuration of radiation-sensitive elements. Such an arrangement permits the speeding up of the measurement due to the smaller number of radiation-sensitive elements 40 in the radiation sensor 4 according to the invention, because, in matrix sensors, the values measured by each radiation-sensitive element 40 are calculated separately. Although as a rule the matrix configuration of radiation-sensitive elements is from the point of view of the measurement speed and ease of processing of the output signal less suitable than a radiation sensor 4 fitted with one row of radiation-sensitive elements 40, there exist cases in which such configuration of the radiation-sensitive elements 40 is more advantageous than the single row arrangement.

It will be appreciated by those skilled in the art that various modifications and variations can be made in the present invention without departing from the scope of the invention. It is intended that the present invention include such modifications and variations as come within the scope of the appended claims and their equivalents.

What is claimed is:

1. A device for contactless measurement of a linear textile formation, said device comprising:
   a radiation source for generating a radiation flux;
   a radiation sensor positioned proximal to said radiation source, said radiation flux receivable by said radiation sensor as said linear textile formation travels between said radiation source and said radiation sensor;
   a plurality of radiation-sensitive elements disposed within said radiation sensor, said plurality of radiation-sensitive elements aligned in at least one row with each of said radiation-sensitive elements larger in length in a direction of travel of said linear textile formation than in width in a direction normal to said direction of travel of said linear textile formation, whereby said length of said radiation-sensitive elements are inferior to the length of the smallest defect required to be detected in said linear textile formation, such that said length of said radiation-sensitive elements are between about 15 µm and about 200 µm; and
   said plurality of radiation-sensitive elements measuring at least one property of said linear textile formation based on at least one of a degree of irradiation sensed by said radiation-sensitive elements and a number of radiation-sensitive elements being overshadowed by said linear textile formation as said radiation flux is received by said radiation sensor.

2. A device as in claim 1, wherein said radiation sensor is a CMOS optical sensor.

3. A device as in claim 1, wherein said radiation sensor is a CCD sensor.

4. A device as in claim 1, wherein said radiation sensor contains at least two rows of radiation-sensitive elements mutually reset in said direction normal to said direction of travel of said linear textile formation.

* * * * *